US009023385B2

(12) United States Patent
Lee et al.

(10) Patent No.: US 9,023,385 B2
(45) Date of Patent: May 5, 2015

(54) PHARMACEUTICAL USE OF 2-(4-MORPHOLINOANILINE)-6-CYCLOHEXYL AMINOPURINE AND/OR SALT THEREOF FOR IMPROVING LIVER FUNCTIONING

(71) Applicants: Ka Ho Kenneth Lee, Zhangzhou (CN); Ruohan Chen, Zhangzhou (CN); Zhibo Hou, Zhangzhou (CN); Quanwei Pan, Zhangzhou (CN)

(72) Inventors: Ka Ho Kenneth Lee, Zhangzhou (CN); Ruohan Chen, Zhangzhou (CN); Zhibo Hou, Zhangzhou (CN); Quanwei Pan, Zhangzhou (CN)

(73) Assignee: Zhangzhou Pien Tze Huang Pharmaceutical Co., Ltd., Zhangzhou (CN)

( * ) Notice: Subject to any disclaimer, the term of this patent is extended or adjusted under 35 U.S.C. 154(b) by 0 days.

(21) Appl. No.: 14/094,064

(22) Filed: Dec. 2, 2013

(65) Prior Publication Data

US 2014/0086984 A1     Mar. 27, 2014

Related U.S. Application Data

(63) Continuation-in-part of application No. PCT/CN2012/073501, filed on Apr. 3, 2012.

(30) Foreign Application Priority Data

Jun. 1, 2011 (CN) .......................... 2011 1 0146859

(51) Int. Cl.
*A61K 9/127* (2006.01)
*A61K 31/5377* (2006.01)

(52) U.S. Cl.
CPC .......... *A61K 31/5377* (2013.01); *Y10S 514/893* (2013.01); *A61K 9/127* (2013.01)

(58) Field of Classification Search
None
See application file for complete search history.

(56) References Cited

U.S. PATENT DOCUMENTS

2007/0167504 A1* 7/2007 Rossignol ...................... 514/370
2008/0193512 A1* 8/2008 Niitsu et al. ................... 424/450
2010/0172893 A1* 7/2010 Anderson et al. .......... 424/130.1

FOREIGN PATENT DOCUMENTS

WO    WO-2008060535 A2    5/2008
WO    WO 2008060535 A2 *  5/2008

OTHER PUBLICATIONS

R Bataller, DA Brenner. "Liver Fibrosis." The Journal of Clinical Investigation, vol. 115 No. 2, Feb. 2005, pp. 209-218.*
SM Berge, LD Bighley, DC Monkhouse. "Pharmaceutical Salts." Journal of Pharmaceutical Sciences, vol. 66 No. 1, Jan. 1977, pp. 1-19.*
M Perreira, JK Jiang, AM Klutz, ZG Guo, A Shainberg, C Lu, CJ Thomas, KA Jacobson. ""Reversine" and Its 2-Substituted Adenine Derivatives as Potent and Selective A3 Adenosine Receptor Antagonists." Journal of Medicinal Chemistry, vol. 48, 2005, pp. 4910-4918.*
Li et al. "Reversine Inhibits the Hyper-Expression of Anti-Apoptotic Protein BRE, TNFR1, and Autophagy Protein Beclin1 in Liver Fibrosis in Mice." Guangdong Medical Journal, vol. 32 No. 16, Aug. 2011, pp. 1941-1944.*
Li et al., Reversine inhibits the hyper-expression of anti-apoptotic protein BRE, TNFR1 and autophagy protein Beclin1 in liver fibrosis in mice, Guangdong Medical Journal, Aug. 2011, vol. 32, No. 15, pp. 1941-1944.

* cited by examiner

*Primary Examiner* — Frederick Krass
*Assistant Examiner* — Isaac Shomer
(74) *Attorney, Agent, or Firm* — Rabin & Berdo, P.C.

(57) ABSTRACT

A method of treating a patient to improve liver functioning includes providing a drug composed of at least one of pharmaceutical 2-(4-morpholinoaniline)-6-cyclohexyl aminopurine and a pharmaceutically acceptable salt thereof; and administering the drug to the patient in a manner and dosage effective to improve liver functioning. The 2-(4-morpholinoaniline)-6-cyclohexyl aminopurine can inhibit the activated hepatic stellate cells from synthesizing and expressing collagens and other extracellular matrix proteins including MMPs and TIMPs, and so it can inhibit liver fibrosis. In the liver, it can inhibit collagen synthesis and expression, and therefore reverse and treat hepatitis and liver cirrhosis effectively. Also discloses is a method for preparing drugs for treating infective hepatitis, non-infectious hepatitis, liver injury, liver cirrhosis, liver cancer and liver fibrosis, and improving t liver functioning, in which the compound and/or salt thereof is used optionally or in combination with a target molecule or carrier comprising a vitamin A-coupled liposome.

4 Claims, 3 Drawing Sheets

PHARMACEUTICAL USE OF 2-(4-MORPHOLINOANILINE)-6-CYCLOHEXYL AMINOPURINE AND/OR SALT THEREOF FOR IMPROVING LIVER FUNCTIONING

CROSS-REFERENCE TO RELATED APPLICATION

This application is a continuation of co-pending International Application No. PCT/CN2012/073501, with an international filing date of Apr. 3, 2012, now is pending, the subject matter of which is incorporated herein by reference, and claims the foreign priority benefit under 35 USC 119 of Chinese Application No. 201110146859.X, filed on Jun. 1, 2011, the subject matter of which is incorporated herein by reference.

FIELD OF THE INVENTION

The present invention relates to the pharmaceutical use of 2-(4-morpholinoaniline)-6-cyclohexyl aminopurine and pharmaceutically acceptable salt or derivative thereof, especially to a new use in the pharmaceutical field.

BACKGROUND OF THE INVENTION

Hepatitis is one of the most endemic disease in the world including China, the etiology of hepatitis is divided into infective and non-infective, infective hepatitis comprising chronic hepatitis B (HBV), hepatitis C virus (HCV) and hepatitis D virus (HDV), schistosomiasis and so on; non-infective hepatitis comprising inborn metabolic error (such as hepatolenticular degeneration, hemachrommatosis, alpha-1-antitrypsin deficiency), chemistry metabolic error (such as chronic alcoholic hepatitis and chronic drug-induced hepatitis) and autoimmune hepatitis, primary biliary cirrhosis and primary sclerosing cholangitis. Therefore, hepatitis virus infection is a condition that covers large area of the world (mainly in the third world countries) and there are billions of people are infected. The population of China has reached to 1.3 billion and it has been estimated that more than 10% of Chinese are infected with hepatitis. In China, hepatitis patients are 85%-90% HBV-positive, but in Japan, Euro and North America, the hepatitis patients are HCV-positive. The relative risk of acquiring liver cancer in those who is infected HBsAg positive is 10 to 50 times higher than those who are HBsAg-negative. Although we have hepatitis B vaccine, there is no hepatitis C vaccine yet, so vaccines cannot overall protected against infectious hepatitis. In addition, many Chinese like to drink and smoke, with other environmental or genetic causes, hepatitis may develop into liver fibrosis, cirrhosis, even liver cancer, so that there is a high incidence rate of liver cancer in China. Hepatitis and liver cancer patients are suffering from illness, and the cost of medical care is out of sight, the interferon to cure hepatitis and liver cancer, interleukin and antiviral drugs are too expansive, and the effects are barely satisfactory. It causes personal and societal economic loss of thousands of billions, therefore it is necessary to develop new drugs and new therapy to meet the present needs of patients with liver disease.

The present invention of a heterocyclic purine molecule compounds, 2-(4-morpholinoaniline)-6-cyclohexyl aminopurine, and pharmaceutically acceptable salt or derivative thereof can inhibit activated hepatic stellate cells from synthesizing type I collagen. The compounds can be used in preparing effective drugs for treating hepatic fibrosis and hepatitis. The constitutional formula is 2-(4-morpholinoaniline)-6-cyclohexyl aminopurine, alternately named Reversine, is as below:

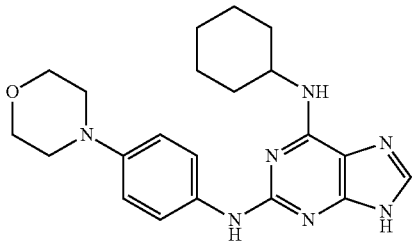 [SMILES: c1nc2c(NC3CCCCC3)nc(Nc3ccc(N4CCOCC4)cc3)nc2[nH]1]

The molecular formula of the small molecule compound is $C_{21}H_{27}N_7O$, and the molecular weight is 393.

SUMMARY OF THE INVENTION

The objective of the present invention is to provide with a new use for heterocyclic purine molecule compounds, 2-(4-morpholinoaniline)-6-cyclohexyl aminopurine, and pharmaceutically acceptable salt or derivative thereof, that is to say, it provides with a new pharmaceutical use.

The present invention relates to a pharmaceutical use of 2-(4-morpholinoaniline)-6-cyclohexyl aminopurine and pharmaceutically acceptable salt or derivative thereof for preparing drugs for treating or preventing hepatitis.

In another preferred embodiment, it relates to a pharmaceutical use of 2-(4-morpholinoaniline)-6-cyclohexyl aminopurine and pharmaceutically acceptable salt or derivative thereof for preparing drugs for treating or preventing non-infectious hepatitis.

In another preferred embodiment, it relates to a pharmaceutical use of 2-(4-morpholinoaniline)-6-cyclohexyl aminopurine and pharmaceutically acceptable salt or derivative thereof for preparing drugs for treating or preventing liver fibrosis.

In another preferred embodiment, it relates to a pharmaceutical use of 2-(4-morpholinoaniline)-6-cyclohexyl aminopurine and pharmaceutically acceptable salt or derivative thereof for preparing drugs for treating or preventing liver cirrhosis.

In another preferred embodiment, it relates to a pharmaceutical use of 2-(4-morpholinoaniline)-6-cyclohexyl aminopurine and pharmaceutically acceptable salt or derivative thereof for preparing drugs for treating or preventing liver cancer.

In another preferred embodiment, it relates to a pharmaceutical use of 2-(4-morpholinoaniline)-6-cyclohexyl aminopurine and pharmaceutically acceptable salt or derivative thereof for preparing drugs for treating or preventing liver fibrosis.

In another preferred embodiment, it relates to a pharmaceutical use of 2-(4-morpholinoaniline)-6-cyclohexyl aminopurine and pharmaceutically acceptable salt or derivative thereof for preparing drugs for protecting and improving the liver function.

In another preferred embodiment, it also relates to a pharmaceutical use of 2-(4-morpholinoaniline)-6-cyclohexyl aminopurine and pharmaceutically acceptable salt or derivative thereof for preparing drugs for treating or preventing infective hepatitis, non-infectious hepatitis, liver injury, liver cirrhosis, liver cancer and liver fibrosis, and protecting and improving the liver function, the compound is used in combination with a target molecule or carrier comprising a vitamin A-coupled liposome.

The present invention of 2-(4-morpholinoaniline)-6-cyclohexyl aminopurine and pharmaceutically acceptable salt or derivative thereof can be prepared to be conventional pharmaceutical preparations, such as tablets, capsules, injections or liposome. Or it can be used in combination with a target molecule or carrier comprising a vitamin A-coupled liposome.

Unless specified otherwise, the terms and scientific terminologies here are the same as a person skilled in the relevant field of technology understands.

The advantages of the present invention are as below:

1. The present invention provides a new medical use of an existing compound 2-(4-morpholinoaniline)-6-cyclohexyl aminopurine and pharmaceutically acceptable salt or derivative thereof, it opens up a new applicability field.

2. 2-(4-morpholinoaniline)-6-cyclohexyl aminopurine can inhibit activated hepatic stellate cells from synthesizing to Type I Collagen. Moreover, the hepatic stellate cells are inactivated. It shows that it can treat and prevent infective hepatitis, non-infectious hepatitis, liver injury, liver cirrhosis, liver cancer and liver fibrosis, and protects and improves the liver function.

3. 2-(4-morpholinoaniline)-6-cyclohexyl aminopurine can directly inhibit collagen synthesis and expression in the mouse model, to prevent liver fibrosis progression, so potentially it can reduce incidence of the disease and death rate.

4. The compound is readily sourced and simple to prepare.

BRIEF DESCRIPTION OF THE DRAWINGS

FIGS. 2A & 2B illustrate the ability of activated hepatic stellate cells to synthesize to Type I Collagen in control group.

FIGS. 2C & 2D illustrate that 2-(4-morpholinoaniline)-6-cyclohexyl aminopurine treatment of activated hepatic stellate cells for 3 days inhibited these cells from expressing and synthesizing Type I Collagen.

FIG. 3A illustrates activated hepatic stellate cells can express and synthesize matrix metalloproteinases-2 (MMP-2) in the control group.

FIG. 3C illustrates activated hepatic stellate cells can express and synthesize matrix metalloproteinases-3 (MMP-3) in the control group.

FIG. 3B illustrates 2-(4-morpholinoaniline)-6-cyclohexyl aminopurine treatment of activated hepatic stellate cells for 3 days, inhibited them from expressing and synthesizing and MMP-2.

FIG. 3D illustrates 2-(4-morpholinoaniline)-6-cyclohexyl aminopurine treatment of activated hepatic stellate cells for 3 days inhibited them from expressing and synthesizing MMP-3.

FIG. 4A illustrates activated hepatic stellate cells can express and synthesize tissue inhibitor of metalloproteinase-2 (TIMP-2) in the control group.

FIG. 4C illustrates activated hepatic stellate cells synthesize and express tissue inhibitor of metalloproteinase-3 (TIMP-3), in the control group.

FIG. 4B illustrates 2-(4-morpholinoaniline)-6-cyclohexyl aminopurine treatment for three days could inhibit activated hepatic stellate cells from expressing and synthesizing TIMP-2.

FIG. 4D illustrates 2-(4-morpholinoaniline)-6-cyclohexyl aminopurine treatment of activated hepatic stellate cells for 3 days inhibited them from expressing and synthesizing TIMP-3.

FIG. 5a illustrates a histological section of a rat liver treated with saline for fifteen days after the $CCl_4$-induction.

FIG. 5b illustrates a histological section of the liver treated with 50 µg/kg of 2-(4-morpholinoaniline)-6-cyclohexyl aminopurine for fifteen days after $CCl_4$-induction.

FIG. 5c illustrates a histological section of the liver treated with 100 µg/kg of 2-(4-morpholinoaniline)-6-cyclohexyl aminopurine for fifteen days after $CCl_4$-induction.

FIG. 5d illustrates a histological section of a 6 week-$CCl_4$ induced liver treated with normal saline for fifteen days.

FIG. 5e illustrates the histological section of the 6 week-$CCl_4$ induced liver treated with 50 µg/kg of 2-(4-morpholinoaniline)-6-cyclohexyl aminopurine for fifteen days.

FIG. 5f illustrates the histological section of the 6 week-$CCl_4$ induced liver treated with 100 µg/kg of 2-(4-morpholinoaniline)-6-cyclohexyl aminopurine for fifteen days.

DETAILED DESCRIPTION OF THE EMBODIMENTS

The First Embodiment: Pharmacological Test

1. The inhibitory action of 2-(4-morpholinoaniline)-6-cyclohexyl aminopurine on activated rat hepatic stellate cells The isolation of the rat hepatic stellate cells: The liver of an adult male Sprague-Dawley rats (500-600 g) were excised out after perfusion with pronase and collagenase. The liver tissue was homogenized and centrifuged. After discontinuous and gradual centrifugation, the purely degree of the original cell suspension reaches to 95%. The cells were then isolated and purified up so that 95% of the cells were hepatic stellate cells. The cells were cultured in DMEM (Dulbecco Meliorated Eagle Medium) with 20% FBS inside culture plates at a cell density of $1.5 \times 10^5$ cells/cm$^2$. After two days incubation, the culture medium was changed and the cell debris was washed and removed.

The culture condition of rat hepatic stellate cells: The rat hepatic stellate cells were cultured in DMEM containing 20% fetal bovine serum (FBS), penicillin (100 U/ml) and streptomycin (100 ug/ml) at 37° C. in 5% $CO_2$. The culture medium was changed for every fourth day. The hepatic stellate cells became activated after ten day in culture and started producing Type-I collagen.

The inhibitory effect of 2-(4-morpholinoaniline)-6-cyclohexyl aminopurine on activated rat hepatic stellate cells: The cells were treated with 5-10 µM of 2-(4-morpholinoaniline)-6-cyclohexyl aminopurine for 24 hours. The treated cells were then collected for Microarrays analysis. The treated cells were also processed for immunofluorescence staining and RT-PCR quantification.

The western blot analysis: The cells are disrupted in 200 μl lysis buffer (50 mM NaCl, 20 mM Tris (trihydroxymethyl aminomethane) pH 7.6, 1% Nonidet P-40, 1× protease inhibitor compounds) for 1 hour at 4° C. After incubation, the lysate was centrifuged at 16,000×g for 10 mins. The supernatant was transferred to a new tube and a protein quantification kit was used to quantify the concentration of proteins in each samples. 25 μg of total protein from each sample was loaded into the 10% SDS PAGE gel for analysis. Collagen-I, MMP-2, MMP-3, TIMP-2 and TIMP-3 mouse monoclonal antibodies (Santa Cruz Lab) were used to analyze the samples. Beta-actin and beta-tubulin monoclonal antibodies (1:1000 diluted) were used as internal control and normalization.

Figure 1:
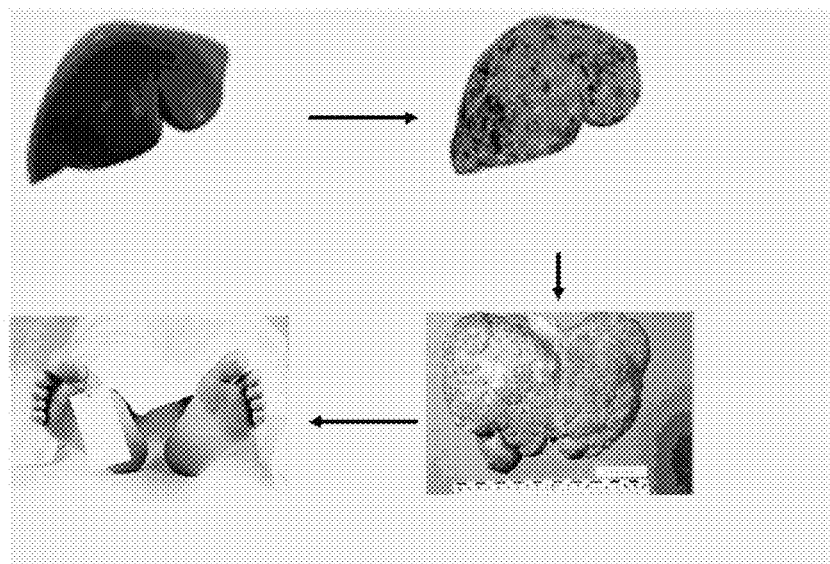
FIG. 1 illustrates the consequences of the pathogenesis of liver fibrosis and cirrhosis leading to disease related death.
Figure 2:
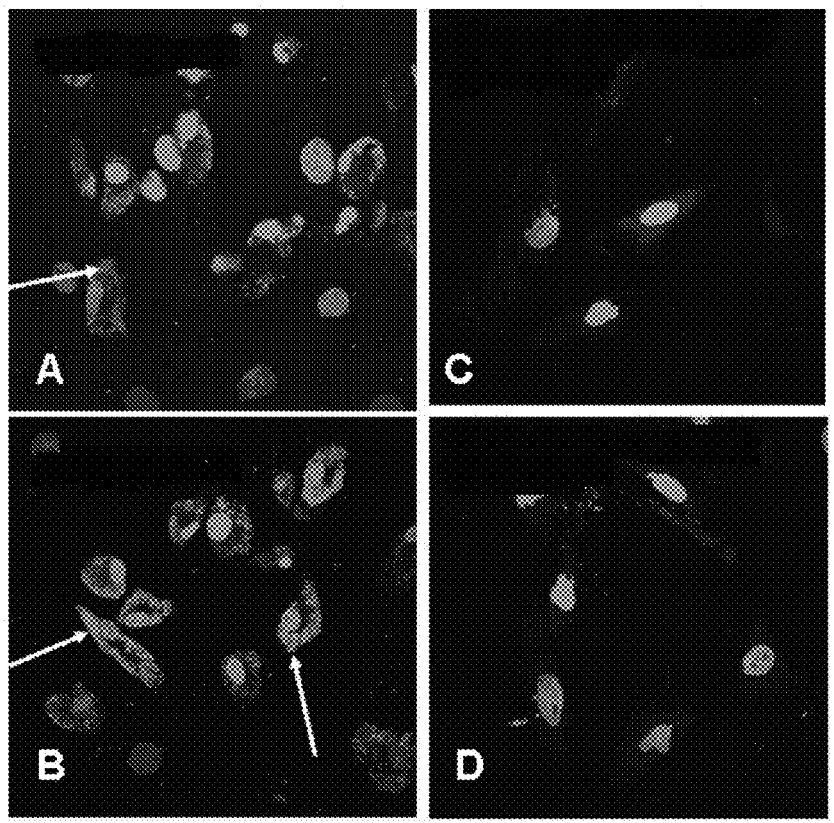
FIG. 2 illustrates that 2-(4-morpholinoaniline)-6-cyclohexyl aminopurine treatment inhibits the activated hepatic stellate cells from expressing and synthesizing Type I Collagen.
Figure 3:
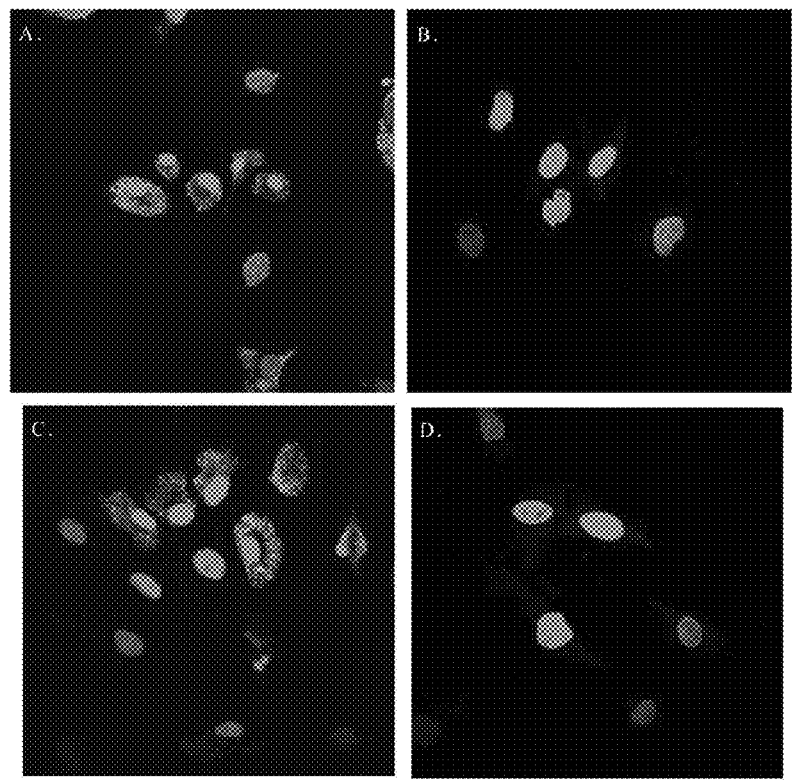
FIG. 3 illustrates 2-(4-morpholinoaniline)-6-cyclohexyl aminopurine treatment inhibits the activated hepatic stellate cells from synthesizing and expressing MMP-2 and MMP-3.
Figure 4:
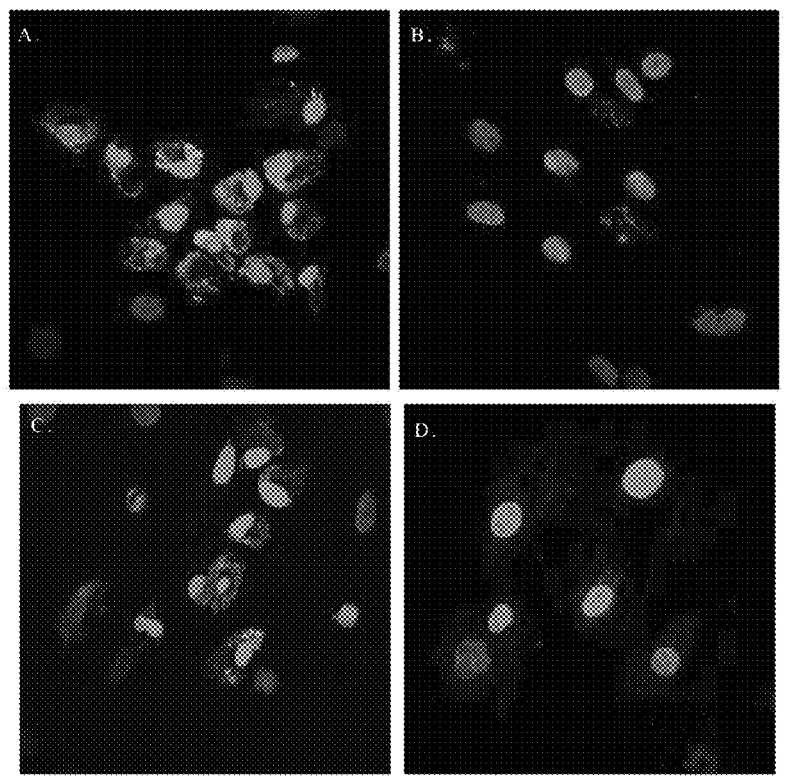
FIG. 4 illustrates 2-(4-morpholinoaniline)-6-cyclohexyl aminopurine treatment of activated hepatic stellate cells for 3 days inhibited them from expressing and synthesizing TIMP-2 and TIMP-3.

Results i. The activated hepatic stellate cells treated with 2-(4-morpholinoaniline)-6-cyclohexyl aminopurine were inhibited from synthesizing and expressing Type I Collagen (as shown in FIG. 2). FIGS. 2A & 2B showed activated hepatic stellate cells could synthesize type-I collagen. FIGS. 2C & 2D revealed that 2-(4-morpholinoaniline)-6-cyclohexyl aminopurine treatment inhibited the activated hepatitis stellate cells from expressing and synthesizing Type-I Collagen.

ii. 2-(4-morpholino aniline)-6-cyclohexyl aminopurine treatment of activated hepatic stellate cells could inhibit them from synthesizing matrix metalloproteinases-2 (MMP-2) and matrix metalloproteinases-3 (MMP-3) (as shown in FIG. 3). FIGS. 3A & 3C showing untreated activated hepatic stellate cells can synthesize MMP-2 and MMP-3. In contrast, FIGS. 3B & 3D revealed 2-(4-morpholinoaniline)-6-cyclohexyl aminopurine treatment suppressed activated hepatic stellate cells from expressing and synthesizing MMP-2 and MMP-3.

iii. 2-(4-morpholinoaniline)-6-cyclohexyl treatment inhibited the activated hepatic stellate cells from synthesizing TIMP-2 and TIMP-3 (as shown in FIG. 4). FIGS. 4A & 4C showed that untreated activated hepatitis stellate cells can synthesize tissue inhibitor of metalloproteinase-2 (TIMP-2) and TIMP-3 in the control group. FIGS. 4B & 4D demonstrated treating the activated hepatic stellate cells with 2-(4-morpholinoaniline)-6-cyclohexyl aminopurine for 3 days could inhibit the cells from producing TIMP-2 and TIMP-3.

2. The effect of 2-(4-morpholinoaniline)-6-cyclohexyl aminopurine treatment in a rat liver fibrosis model.

Figure 5:
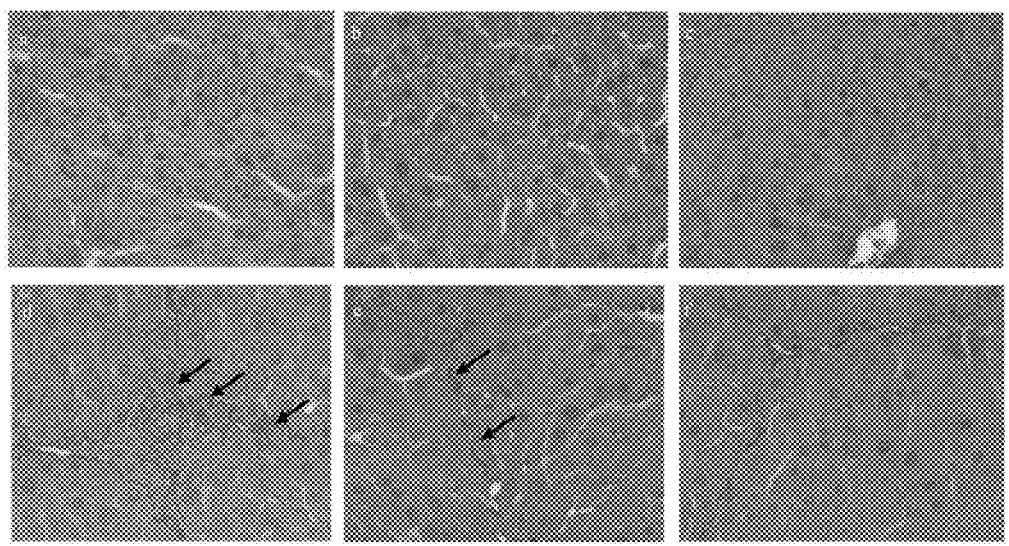
FIG. 5 illustrates histological sections of fibryotic livers isolated from $CCl_4$-induced rats. These fibryotic rats were treated with either saline (control group) or 2-(4-morpholinoaniline)-6-cyclohexyl aminopurine (experimental group).

Twenty-four adult male Sprague-Dawley rats (500-600 g) were divided into 4 groups (n=6), the first group (control) was injected with carbon tetrachloride ($CCl_4$) intraperitonally (i.p.) twice per week for 6 weeks to induce liver fibrosis. The control rats were not treated with 2-(4-morpholinoaniline)-6-cyclohexyl aminopurine. In the second group, the rats were injected with $CCl_4$ i.p. twice per week for 6 weeks and then followed by i.p. injection of 50 μg/kg of 2-(4-morpholinoaniline)-6-cyclohexyl aminopurine twice a week for two weeks after the induction of liver fibrosis. The third group was injected with $CCl_4$ i.p. twice per week for 6 weeks and then followed by i.p. injection of 100 μg/kg of 2-(4-morpholinoaniline)-6-cyclohexyl aminopurine twice a week for two weeks after the induction of liver fibrosis. The fourth group was injected with $CCl_4$ i.p. twice per week for 6 weeks and then followed by i.p. injection of 50 μg/kg of 2-(4-morpholinoaniline)-6-cyclohexyl aminopurine twice a week for four weeks after the induction of liver fibrosis. At the end of the experimentation, the different groups of rats were sacrificed and samples of the liver were collected and fixed in 4% buffered formalin for 24 hours. Paraffin embedded samples were sectioned for histology and immunohistochemistry. Liver samples were also collected and stored in −20° C. for Western Blot Analysis and RT-PCR quantification. FibroIndex Analysis was performed to demonstrate the effectiveness of 2-(4-morpholinoaniline)-6-cyclohexyl aminopurine in inhibiting liver fibrosis progression in vivo. The results show that 2-(4-morpholinoaniline)-6-cyclohexyl aminopurine treatment were effective in inhibiting collagen synthesis in the rat $CCl_4$-induction liver fibrosis model as shown in FIG. 5.

The second embodiment: Preparation of vitamin A-coupled liposome with containing 2-(4-morpholinoaniline)-6-cyclohexyl aminopurine. Add double distilled water to freeze-drying cationic liposome of liposome (O,O'-ditetradecanoyl-N-(α-trimethyl ammonioacetyl) diethanolamine chloride (DC-6-14), cholesterol and dioleoylphosphatidylethanolamine mixed in a ratio of 4:3:3), make the concentration of the (DC-16-4) being 1 mM, shake before using. Dissolve 200 nmol of vitamin A in the DMSO, then in 25° C., mix it with 100 nmol of the above cationic liposome suspension in 1.5 mL tube at 25° C., shake to get vitamin A liposome. Put 2-(4-morpholinoaniline)-6-cyclohexyl aminopurine into the vitamin A liposome, the ratio of 2-(4-morpholinoaniline)-6-cyclohexyl aminopurine to DC-16-4 is 1:11.5 (mol/mol) and the ratio of 2-(4-morpholinoaniline)-6-cyclohexyl aminopurine to vitamin A liposome is 1:1 (wt/wt). The free vitamin A and unabsorbed 2-(4-morpholinoaniline)-6-cyclohexyl aminopurine were separated from the liposome mixture using a microfilter system. The liposome suspension was added to a filter for centrifugation three times at 1500 g at 25° C. The vitamin A-coupled liposome containing 2-(4-morpholinoaniline)-6-cyclohexyl aminopurine was then obtained. The composition ratio of 2-(4-morpholinoaniline)-6-cyclohexyl aminopurine vitamin A/liposome is shown in FIG. 2. The composition of 2-(4-morpholinoaniline)-6-cyclohexyl aminopurine vitamin A/liposome is listed in Table 1.

TABLE 1

The composition of 2-(4-morpholinoaniline)-6-cyclohexyl aminopurine vitamin A/liposome

| Preparation | composition |
| --- | --- |
| liposome | Positive ion oil (DC-6-14): DOPC: Cholesterol (mixed at a ratio of 4:3:3) |
| vitamin A | vitamin A: liposome (mixed at a ratio of 2;1) |
| 2-(4-morpholinoaniline)-6-cyclohexyl aminopurine | 2-(4-morpholinoaniline)-6-cyclohexyl aminopurine (2-50 μM)/vitamin A/liposome mixture |

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

INDUSTRIAL APPLICABILITY

The present invention provides a new use of 2-(4-morpholinoaniline)-6-cyclohexyl aminopurine and pharmaceutically acceptable salt or derivative thereof. Also discloses is a method for preparing drugs for treating or preventing liver fibrosis, hepatitis, liver injury, liver cirrhosis and liver cancer, thus protecting and improving the liver function.

What is claimed is:

1. A method of treating a patient for liver fibrosis comprising:
administering an effective amount of a drug comprising at least one of 2-(4- morpholinoaniline)-6-cyclohexyl aminopurine and a pharmaceutically acceptable salt thereof to a patient suffering from liver fibrosis.

2. A method of treating a patient for liver fibrosis comprising:
  administering an effective amount of a drug comprising at least one of 2-(4-morpholinoaniline)-6-cyclohexyl aminopurine and a pharmaceutically acceptable salt thereof; and optionally a targeting molecule or carrier comprising a vitamin A-coupled liposome;
  to a patient suffering from liver fibrosis.

3. The method according to claim 1, wherein the drug comprises at least one of pharmaceutical 2-(4-morpholinoaniline)-6-cyclohexyl aminopurine and a pharmaceutically acceptable salt thereof; and a target molecule or carrier comprising a vitamin A-coupled liposome.

4. The method according to claim 2, wherein the drug comprises said pharmaceutically acceptable salt; and a target molecule or carrier comprising a vitamin A-coupled liposome.

\* \* \* \* \*